United States Patent
Bassi et al.

(10) Patent No.: US 9,238,618 B2
(45) Date of Patent: Jan. 19, 2016

(54) PRODUCTION OF POLYOLS USING DISTILLERS GRAINS AND PROTEINS AND LIGNIN EXTRACTED FROM DISTILLERS GRAINS

(71) Applicants: MGPI Processing, Inc., Atchison, KS (US); Pittsburg State University, Pittsburg, KS (US)

(72) Inventors: Sukh Bassi, Overland Park, KS (US); Michael Douglas Parker, Shawnee, KS (US); Mihail Ionescu, Pittsburg, KS (US); Zoran Petrovic, Pittsburg, KS (US)

(73) Assignees: MGPI Processing, Inc., Atchison, KS (US); Pittsburg State University, Pittsburg, KS (US)

( * ) Notice: Subject to any disclaimer, the term of this patent is extended or adjusted under 35 U.S.C. 154(b) by 0 days.

(21) Appl. No.: 14/516,414

(22) Filed: Oct. 16, 2014

(65) Prior Publication Data
US 2015/0038665 A1    Feb. 5, 2015

Related U.S. Application Data

(63) Continuation of application No. 13/757,179, filed on Feb. 1, 2013, now abandoned.

(60) Provisional application No. 61/751,510, filed on Jan. 11, 2013.

(51) Int. Cl.
| | |
|---|---|
| *C08L 71/02* | (2006.01) |
| *C08L 5/16* | (2006.01) |
| *C08B 37/16* | (2006.01) |
| *C08H 6/00* | (2010.01) |
| *C12F 3/10* | (2006.01) |
| *C08H 7/00* | (2011.01) |
| *C07C 231/14* | (2006.01) |
| *C08L 97/00* | (2006.01) |
| *C08L 75/16* | (2006.01) |
| *C08G 18/38* | (2006.01) |
| *C08G 18/76* | (2006.01) |

(52) U.S. Cl.
CPC .......... *C07C 231/14* (2013.01); *C08G 18/3825* (2013.01); *C08G 18/7664* (2013.01); *C08G 18/7671* (2013.01); *C08H 6/00* (2013.01); *C08L 75/16* (2013.01); *C08L 97/005* (2013.01); *C12F 3/10* (2013.01)

(58) Field of Classification Search
None
See application file for complete search history.

(56) References Cited

U.S. PATENT DOCUMENTS

| | | | | |
|---|---|---|---|---|
| 2,143,360 | A * | 1/1939 | Needle | 435/139 |
| 3,738,994 | A * | 6/1973 | Fisher | 548/309.7 |
| 3,957,702 | A * | 5/1976 | Molotsky et al. | 521/168 |
| 4,585,858 | A * | 4/1986 | Molotsky | 536/4.1 |
| 5,665,152 | A * | 9/1997 | Bassi et al. | 106/145.1 |
| 6,025,452 | A * | 2/2000 | Kurple | 527/301 |
| 6,107,433 | A * | 8/2000 | Petrovic et al. | 528/1 |
| 6,433,121 | B1 * | 8/2002 | Petrovic et al. | 528/1 |
| 6,573,354 | B1 * | 6/2003 | Petrovic et al. | 528/1 |
| 6,686,435 | B1 * | 2/2004 | Petrovic et al. | 528/44 |
| 2007/0135536 | A1 * | 6/2007 | Mohanty et al. | 524/47 |
| 2007/0175793 | A1 * | 8/2007 | Narine et al. | 208/49 |

FOREIGN PATENT DOCUMENTS

WO     WO 2010020903 A1 *   2/2010   ........... C07C 41/03

* cited by examiner

*Primary Examiner* — Peter A Salamon
(74) *Attorney, Agent, or Firm* — Hovey Williams LLP; Gregory J. Skoch

(57) ABSTRACT

Processes for the production of polyols from sources such as dried distillers grains plus solubles (DDGS) make use of a two-stage reaction scheme. In the first stage, the proteinaceous starting material is reacted with an aminating agent, such as diethanolamine (DEOA), to generate amino-amides and amides. These products are then reacted with an alkoxylating agent, preferably a substituted or unsubstituted epoxide to yield polyols. These polyols may be further reacted with isocyanates to give low-cost rigid polyurethane foams. In alternate forms, lignin may be directly converted to polyols by reaction with an alkoxylating agent, optionally followed by reaction with an isocyanate to produce polyurethanes.

55 Claims, No Drawings

PRODUCTION OF POLYOLS USING DISTILLERS GRAINS AND PROTEINS AND LIGNIN EXTRACTED FROM DISTILLERS GRAINS

RELATED APPLICATION

This application is a continuation of pending U.S. patent application Ser. No. 13/757,179, filed Feb. 1, 2013, which claims the benefit of U.S. Provisional Patent Application No. 61/751,510, filed Jan. 11, 2013. Each application is incorporated by reference herein in its entirety.

BACKGROUND OF THE INVENTION

1. Field of the Invention

The present invention is broadly concerned with processes for the production of polyols from proteinaceous and/or fibrous (e.g., lignin) components, and processes for reacting such polyols with isocyanates to produce polyurethanes. More particularly, the invention is concerned with processes wherein a proteinaceous component, and especially a distillers grain product, is reacted with an amine under conditions to generate amino-amides and amides from the protein and lignin fractions of the distillers grain product, and thereupon reacting such aminated products with an alkoxylating agent to generate polyols. Alternately, lignin from any source such as pulp byproducts may be directly alkoxylated to form lignin polyols. However produced, the polyols may then be recovered or reacted with isocyanates to yield polyurethanes.

2. Description of the Prior Art

Distillers grain products are byproduct materials resulting from the fermentation of starch (usually corn starch) to ethanol. These products are generally classified as wet distillers grains (WDG) and dried distillers grains with solubles (DDGS). WDG contains primarily unfermented grain residues (protein, fiber, lipids, and up to 70% moisture). Accordingly, WDG has a shelf life of only 4-5 days and, owing to the high moisture content thereof, transport is usually viable only within 20 km of the ethanol production facility. On the other hand, DDGS is a product that has been dried with concentrated thin stillage to a relatively low moisture content. DDGS has an almost indefinite shelf life and may be economically shipped to remote markets. Therefore, the primary distillers grain products are DDGS.

DDGS contains from about 28-32% protein, from about 9.4-11% lipid, from about 32-40% neutral detergent fiber (cellulose, hemicellulose, lignin), from about 15.2-17.9% acid detergent fiber, from about 9-11.8% starch, from about 4-13.2% ash, and from about 10-12% water, where all percentages are on a weight basis, with the total weight of the DDGS being 100% by weight. The high levels of nutrients in DDGS are digestible, and are useful for animal feeds. Accordingly, it is well known that DDGS are used in beef and dairy diets, and in swine and poultry diets as well. It is also noteworthy that DDGS contain many hydroxyl- and amino-containing compounds.

Lignin is the second most abundant source of carbon on earth, after cellulose and hemicellulose. Lignin is available in enormous quantities as a result of pulp industry practices, but only 1-2% from lignin is used for technical applications (binders, surfactants, phenol-formaldehyde resins etc.). The remainder of the lignin is used primarily as a fuel source. Lignin is present in DDGS in small quantities, around 3-4% by weight, and has phenolic and aliphatic hydroxyl groups.

A review of the prior art reveals only two processes for the transformation of DDGS into liquids, namely Xu et al., *Liquifaction of Corn Distillers Grains with Solubles (DDGS) in Hot Compressed Phenol*, Bioresources, 3(2), 363-382 (2008), and Yu et al., *Atmospheric Pressure Liquifaction of Dried Distillers Grains (DDG) and Making Polyurethane Foams from Liquified DDG*, Appl., Biochem Biotechnol, 148: 235-243 (2008). The latter article teaches that dried distillers grains were treated under acidic conditions at atmospheric pressure, using ethylene carbonate or ethylene glycol as solvents and with sulfuric acid catalyst. The resultant polyols were separated and treated with methylene diphenyl diisocyanate in the presence of catalyst, surfactant, and blowing agent, in order to produce polyurethane foam.

SUMMARY OF THE INVENTION

The present invention in one aspect is directed to new processes for the low-cost production of polyols using conventional equipment. Broadly speaking, the processes comprise the steps of first reacting a proteinaceous component selected from the group consisting of distillers grains, polyamides, and mixtures thereof, with an amine under reaction conditions to generate amino-amides and amides. Thereupon, these reaction products are reacted with an alkoxylating agent to generate polyols, which may be separated or further reacted with an isocyanate to give rigid polyurethane foams, using well-developed technologies.

Preferably, the proteinaceous starting material is DDGS, whereas the aminating reactant used in the first step is a secondary amine, and especially diethanolamine (DEOA). Other proteinaceous sources include human or animal-derived proteins or polyamides. Advantageously, the second alkoxylating step makes use of a substituted or unsubstituted epoxide, especially propylene oxide and ethylene oxide, and mixtures thereof.

The rigid foam polyurethanes produced using the polyols of the invention have high functionalities of around 3-8 hydroxyl groups/mole, and the polymer chains bearing only one hydroxyl group are short. Thus, the invention gives considerable added value to otherwise low-cost proteinaceous materials with minimum additional cost for processing difficulty.

Alternately, polyols may be produced by the direct alkoxylation of the phenolic and aliphatic hydroxyl groups of lignin with alkylene oxide(s) (usually propylene and/or ethylene oxide) in the presence of catalysts to create lignin polyols. The alkoxylation catalysts are normally tertiary amines with low steric hindrances, e.g., trimethylamine, dimethylaminoethanol, dimethyl cyclohexylamine, imidazole and N-Methyl imidazole, tetramethylguanidine. Tetramethylguanidine, an organic superbase, is a very efficient alkoxylation catalyst and need not be removed from the resulting lignin polyols during subsequent reaction with isocyanates to create polyurethanes. The lignin starting material may be the lignin fraction of DDGS, lignin extracted from DDGS, or from any other convenient source, such as wood, plants, or pulp industry byproducts.

DETAILED DESCRIPTION OF THE PREFERRED EMBODIMENTS

In one preferred form of the present invention, solid DDGS is first reacted with an appropriate amine under reaction conditions to liquify the DDGS and to transform the proteinaceous fractions of the DDGS into amino-amides and amides. The amine reactants are usually primary or secondary amines, with secondary amines being preferred, and with DEOA being the most preferred amine.

The amines are preferably selected from the group consisting of amines having the formula

wherein R1 is selectively and individually selected from the group consisting of H, C2-C12 straight and branched chain alkyl and alkenyl groups each having at least one hydroxyl group, and R2 is selectively and individually selected from the group consisting of C2-C12 straight and branched chain alkyl and alkenyl groups each having at least one hydroxyl group.

This initial reaction is carried out at a temperature of from about 150-250° C. (most preferably about 190-200° C.), and a pressure of from about 400-700 psi (most preferably from about 450-500 psi). The ratio of DDGS to amine being from about 0.5-3 (more preferably from about 1-1.2).

The second alkoxylation reactions are advantageously carried out in the absence of catalysts, and at temperatures of from about 80-150° C. (more preferably from about 100-120° C.), and pressures of from about 25-80 psi (more preferably from about 40-60 psi). The alkoxylating agent is preferably selected from the group consisting of epoxides having the formula

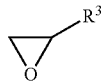

wherein R3 is selected from the group consisting of H, and C1-C6 straight or branched chain alkyl and alkenyl groups. The most preferred epoxides are propylene oxide, ethylene oxide, and mixtures thereof.

The alkoxylated reaction products are normally polyols having hydroxyl numbers on the order of 300-800 mg KOH/g (more preferably from about 400-650 mg KOH/g), depending upon the ratios of DDGS/amine reactant/alkoxylating agent.

In order to better understand the chemistry involved in the present invention, preferred and more generalized reaction schemes are provided below for certain fractions of DDGS.

DDGS Protein Fraction Reactions

The first preferred reaction of the protein fraction of DDGS with the preferred secondary amine DEOA generates transamidation reaction products as follows (Scheme 1):

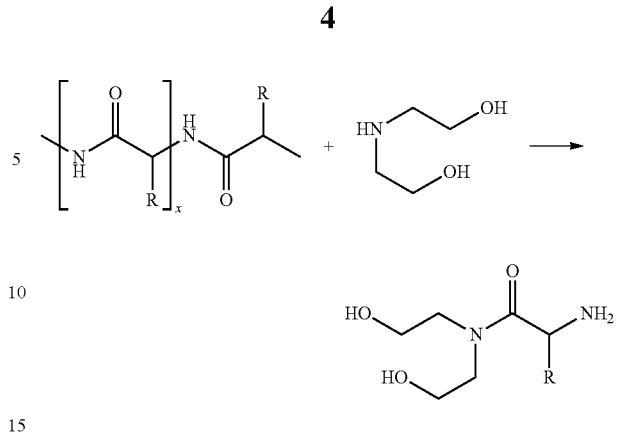

where R is any amino acid side chain, and x>1.

More generally, this reaction is illustrated below (Scheme 1A):

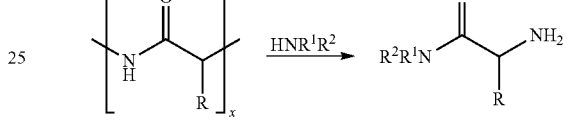

where R is any amino acid side chain, $R^1$ is H, $C_2$-$C_{12}$alkyl with one or more hydroxy groups, $R^2$ is $C_1$-$C_{12}$alkenyl with one or more hydroxy groups, and x>1.

The amino-amides resulting from the initial protein transamidation reactions are converted to polyols using the preferred alkoxylation agent propylene oxide according to the following (Scheme 2):

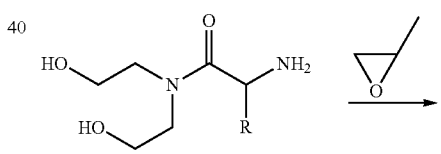

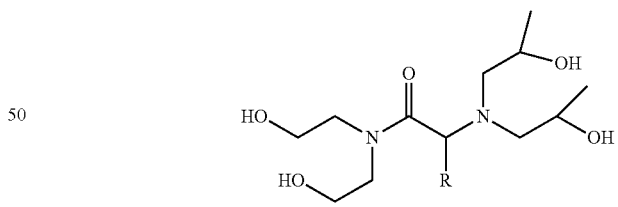

where R is defined above and $R^3$ is $C_1$-$C_6$alkyl.

The more generalized version of this reaction is depicted below (Scheme 2A):

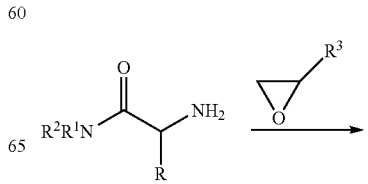

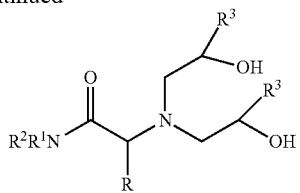

where R, R¹, and R² are defined above, and R³ is $C_1$-$C_6$alkyl.

DDGS Lignin Fraction Reaction

The lignin fraction of DDGS contains phenolic hydroxyl groups and aliphatic hydroxyl groups, and does not appreciably react with the above-described amination reagents. However, the lignin is alkoxylated in order to produce lignin polyols. The preferred reaction using propylene oxide is set forth below (Scheme 3):

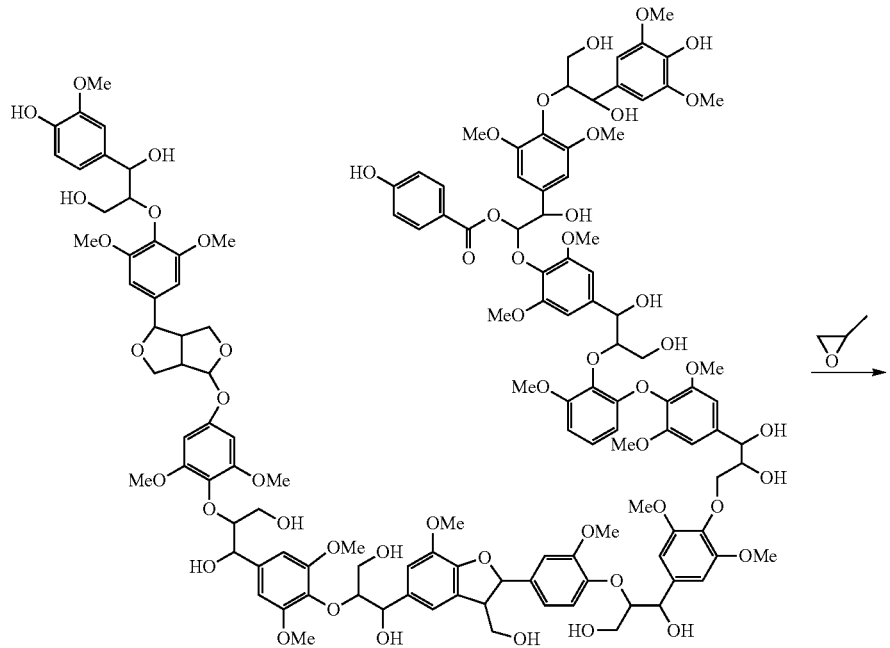

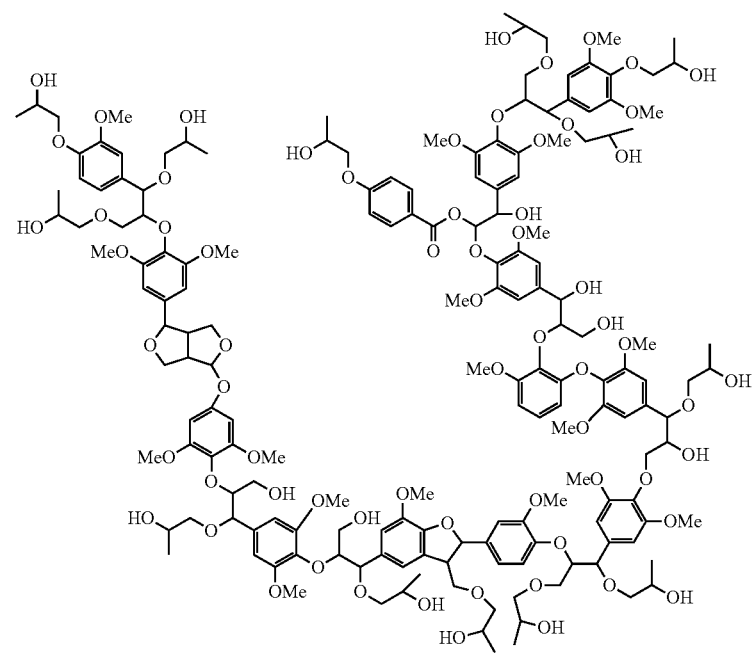

The more generalized lignin reaction is set forth below (Scheme 3A):

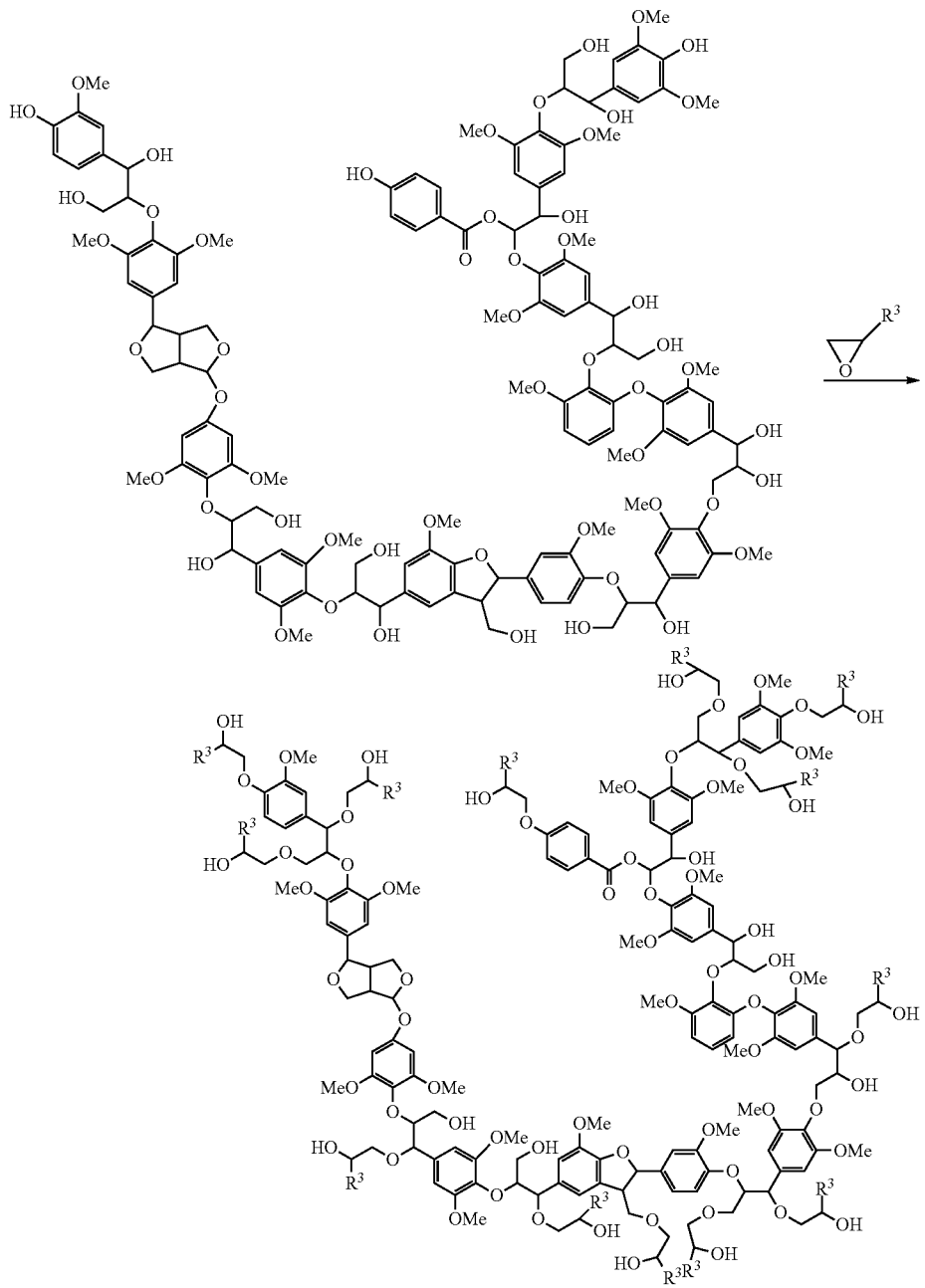

It should be understood that lignins may be a part of DDGS, or an extracted fraction of lignins from DDGS, or any other source of lignins, e.g., wood, cooking liquors generated in wood pulp processing, and plants.

The cellulose, hemicellulose, and starch fractions of DDGS are degraded in the basic reaction conditions to low molecular weight liquid fragments by various reactions, such as dehydration, dehydrogenation, deoxygeneration, decarboxylation, and condensation reactions.

The following examples set forth characteristics of polyols prepared using DDGS and proteins extracted DDGS in accordance with the invention. It is to be understood that these examples are provided by way of illustration only, and nothing therein should be taken as a limitation upon the overall scope of the invention.

Example 1

In this example, 100 g samples of DDGS having a moisture content of about 10-11% by weight were first reacted with DEOA using varying DDGS/DEOA ratios to generate viscous liquid amino-amides via transamidation reactions, followed by reaction of the amino-amides with propylene oxide to generate medium to low viscosity liquid polyols having hydroxyl numbers in the range of from about 400-650 mg KOH/g.

The DDGS/DEOA reaction was carried out at a temperature of from about 190-200° C. in a heated pressure reactor. During this reaction, about 16-20% by weight of the original mass of the DDGS was lost as water and low molecular weight volatile degradation components. As a consequence, the pressure rose in the reactor to about 450-500 psi. The water and volatiles were condensed and collected in Dean Stark trap. Without the water removal step, the propoxylation step would result in low viscosity DDGS polyol products, because water generates low viscosity polypropylene glycols during propoxylation.

The propoxylation reaction was carried out in the absence of catalysts using 200 g of the amino-amides from the first reaction with varying amounts of propylene oxide of from about 120-170 ml (100-140 g) at temperatures of from about 100-120° C. and pressures of from about 40-60 psi. The color of the DDGS polyol material was dark brown to black. After each propoxylation reaction, approximately 15-16% by weight of the polyol material was used as the reaction medium for suspension of the next batch of DDGS. It was found that the DDGS polyol facilitated the conversion of the DDGS to liquid during the subsequent DDGS/DEOA reaction.

The following Table 1 sets forth the characteristics of the final product.

TABLE 1

| Polyol | DDGS (g) | DEOA (g) | DDGS Polyol | Propylene Oxide (g) | OH No. mg KOH/g | Acid Value mg KOH/g | Viscosity @ 25° C. Pa · s |
|---|---|---|---|---|---|---|---|
| DDGS-DEOA-1 | 200 | 100 | — | 100 | 457 | 2.0 | 1.20 |
| DDGS-DEOA-2 | 120 | 100 | — | 100 | 652 | 2.6 | 6.34 |
| DDGS-DEOA-3 | 100 | 100 | — | 100 | 767 | 2.4 | 4.30 |
| DDGS-DEOA-6 | 100 | 100 | — | 100 | 1109 | 6.7 | 0.62 |
| DDGS-DEOA-7 | 100 | 100 | 50 | 120 | 577.4 | 3.0 | 4.12 |
| DDGS-DEOA-8 | 100 | 100 | 50 | 130 | 673.1 | 3.6 | 4.75 |
| DDGS-DEOA-9 | 100 | 100 | 50 | 140 | 744 | 3.2 | 3.28 |
| DDGS-DEOA-10 | 100 | 100 | 50 | 140 | 587.4 | 1.99 | 3.28 |
| DDGS-DEOA-11 | 100 | 100 | 50 | 140 | 577.4 | 3.0 | 4.12 |

Example 2

In this example, zein was extracted from DDGS and was first reacted with DEOA, followed by propoxylation using propylene oxide. In particular, the zein in the first stage reaction was added stepwise to liquid DEOA at a temperature of from about 130-140° C. over 2-3 hours, at a protein/DEOA ratio of from about 1-1.5:1, resulting in a viscous liquid reaction mass. This liquid mass was transferred to a Parr reactor and propoxylated in the absence of catalysts at a temperature of from about 100-120° C. The resulting liquid protein polyols had higher viscosities than those of Example 1, and were brown in color, lighter than the color of the Example 1 DDGS polyols. In two instances, ethylene oxide was added after the propoxylation reaction at a level of about 10-15% by weight ethylene oxide, where the propoxylated polyols are deemed to be 100% by weight, in order to decrease the viscosity of the final protein polyols.

As in the case of Example 1, about 15-16% by weight of the protein polyol product was used as the reaction medium for the next batch of extracted protein to good effect. By the use of this technique it was unnecessary to stepwise add the next batch of extracted protein (i.e., the protein could be added in one step), because the suspension of protein solids in DEOA plus the protein polyol of the preceding reaction was an easily stirable mixture The propoxylation reaction was carried out in the absence of catalysts using 200 g of the amino-amides from the first protein/DEOA reaction, with varying amounts of propylene oxide of from about 120-170 ml (100-140 g) at temperatures of from about 100-120° C. and pressures of from about 40-60 psi.

Table 2 sets forth the results of these tests.

TABLE 2

| Polyols | Zein (g) | DEOA (g) | PO, (EO) (g) | OH No. mg KOH/g | Acid Value mg KOH/g | Viscosity @ 25° C. Pa · s |
|---|---|---|---|---|---|---|
| Zein-DEOA-1 | 200 | 100 | 195 | 635 | 2.1 | 49.5 |
| Zein-DEOA-2 | 100 | 100 | 100 | 421 | 1.8 | 18.8 |
| Zein-DEOA-3 | 200 | 100 | 195 + 52 (EO) | 564 | 2.6 | 11.9 |

TABLE 2-continued

| Polyols | Zein (g) | DEOA (g) | PO, (EO) (g) | OH No. mg KOH/g | Acid Value mg KOH/g | Viscosity @ 25° C. Pa·s |
|---|---|---|---|---|---|---|
| Zein-DEOA-4 | 100 | 100 | 120 | 593 | 0.85 | 21.9 |
| Zein-DEOA-5 | 100 | 100 | 140 | 541.7 | 4.1 | 22.37 |
| Zein-DEOA-6 | 100 | 100 | 140 + 40 (EO) | 575.6 | 1.97 | 14.27 |

While the preferred methods of the invention involve the treatment of DDGS, the invention is not so limited. Indeed, the process hereof can be applied to conversion of essentially any protein to protein polyols. For example, grain-derived proteins from gluten, corn, soy, and potato, can be extracted and subjected to the foregoing reactions. Still further, because proteins are in fact polyamides, the methods hereof can be used for the conversion of any polyamide waste (e.g., polyamide 6, polyamide 11, polyamide 66) to polyols.

The polyols of the invention are very reactive or autocatalytic polyols suitable for "spray" rigid polyurethane foams. Generally, the polyols of the invention can be transformed into rigid polyurethane foams by conventional procedures used for petrochemical polyols. In the first step, the polyol is well mixed with blowing agents, silicon emulsifiers, catalysts such as tertiary amines and tin catalysts, and flame retardants. Next, the homogeneous solution of the polyols with other ingredients are reacted with isocyanates (e.g., crude MDI, polymeric MDI) using a very high efficiency stirrer (3000-5000 rot/min), resulting in a crosslinked rigid polyurethane foam. The resultant foam is rather dark in color, but similar to those of normal rigid polyurethane foams derived from petrochemical polyols. The processes for the preparation of polyols from DDGS, proteins extracted from DDGS, and any other proteins or polyamides have a number of important advantages.

- Polyols based upon DDGS are very cheap and can be generated in huge volumes owing to the wide-scale production of bio-ethanol by fermentation of corn starch.
- The processes can be used in conventional equipment with only very minor modifications.
- DDGS and protein/polyamide polyols can replace 10-50% of petrochemical polyols presently used in the production of rigid polyurethane foams.
- The processes hereof transform low-value proteinaceous sources of vegetable or animal origin, protein wastes, or polyamide wastes, to new valuable polyols.
- The color of rigid polyurethane foams based on DDGS polyols are slightly darker than comparable foams derived from petrochemical polyols. However, polyurethanes developed using proteins, and especially extracted zein, have a color very close or identical with petrochemical polyols polyurethanes.

Example 3

Synthesis of Lignin Polyol (Variant 1—Use of a Portion of Liquid Propylene Oxide to Initially Suspend Solid Lignin)

The formulation used for synthesis of lignin polyols from solid lignin included, in parts by weight:

1) Lignin: 100 parts
2) Glycerol: 50 parts
3) Propylene oxide: 120 parts
4) Tetramethylguanidine (propoxylation catalyst): 1.35 parts Solid lignin (100 parts) was suspended in a liquid mixture consisting in glycerol (50 parts) and a portion of the propylene oxide needed for reaction (50 parts), together with the tetramethylguanidine catalyst (1.35 parts). The reactor was then purged with nitrogen to eliminate air, generating a pressure of 5-10 psi of nitrogen. The reactor was slowly heated to 120-125° C. At a temperature of 90-95° C. an exothermal reaction was observed, and the reactor was indirectly cooled with water using the internal coil of the reactor. Initial pressure at the beginning of the reaction increased to 40-50 psi, but, owing to the consumption of propylene oxide during ring-opening addition to the hydroxyl groups of the lignin and the glycerol, the pressure decreased markedly. At this point, the remainder of the propylene oxide (70 parts) was added stepwise over a period of about 2 hours at 125-130° C. and pressure of 40-60 psi. After the addition of the entire quantity of propylene oxide the reactor was maintained at 120-125° C., under continuous stirring for about 1.5 hours in order to assure complete consumption of any unreacted propylene oxide. The last traces of propylene oxide were removed by vacuum distillation (60-65 mm Hg, and 100-110° C.). The final reaction product was a viscous liquid polyol of dark brown color and having a hydroxyl number of 497 mg KOH/g, an acid value of 1.5 mg KOH/g, and a viscosity of 21.6 Pa·s at 25° C. The resulted lignin polyol had a number average molecular weight (Mn) of 790, a weight average molecular weight (Mw) of 7000, and a polydispersity index (Mw/Mn) of 8.8.

Example 4

Synthesis of Lignin Polyol (Variant 2—Use of Liquid Lignin Polyol to Initially Suspend Solid Lignin)

This synthesis variant employed a quantity of the lignin polyol prepared in accordance with Example 3 as the suspending liquid in lieu of propylene oxide. Lignin polyol, having a similar structure as compared with solid lignin, provided a good compatibility between solid lignin and the liquid reaction mass. In this synthesis, the starting formulation included, in parts by weight:

1) Lignin: 100 parts
2) Glycerol: 50 parts
3) Lignin polyol: 50 parts
4) Propylene oxide: 120 parts;
5) Tetramethylguanidine: 1.3-1.4 parts.

The solid lignin was first suspended in the liquid mixture comprising glycerol and lignin polyol, followed by addition of the catalyst. The reactor was then purged with nitrogen as described in Example 3, giving an inert nitrogen atmosphere of 5-10 psi. The reactor was then heated to 120-125° C., whereupon the propylene oxide was added stepwise over 3-4 hours at 120-125° C. at a pressure of 40-60 psi. After the addition of the entire quantity of propylene oxide, as described in Example 3, the reactor was maintained at 120-125° C., with continuous stirring for a period of about 1.5 hours, in order to consume all unreacted propylene oxide. The last traces of propylene oxide were removed by vacuum distillation (60-65 mm Hg, and 100-110° C.), giving a viscous, dark-brown liquid lignin polyol having a hydroxyl number of 491 mg KOH/g, a viscosity of 20.1 Pa·s at 25° C., and an acid value of 1.34 mg KOH/g. The polyol had a number average molecular weight (Mn) of 910, a weight average molecular weight (Mw) of 8300, and a polydispersity index (Mw/Mn) of 9.1. If desired, approximately 15-16% of this lignin polyol could be used for the next lignin polyol synthesis.

The optimum lignin source for conversion to lignin polyols is organosolv lignin, a very pure lignin obtained by extraction of lignin from wood or from annual plant crops with organic solvents. "Kraft" lignin and "sulfite" lignins derived from the pulp industry are generally less suitable for the preparation of lignin polyols, because these materials have high concentrations of sulfur and sodium. Sodium ions present in these byproduct lignins catalyze side reactions (e.g., trimerization reactions) during conversion of the polyols to polyurethane. High concentrations of sulfur generate strong and unpleasant odors during subsequent processing of the polyols.

Polyurethane foams prepared through isocyanate reactions with lignin polyols are darker in color than the corresponding polyurethane foams prepared using petrochemical-based lignin polyols. However, this is unimportant if the foams are used in contexts where the appearance of the foams is not significant (e.g., as refrigerator or freezer insulation panels).

In the following table, certain characteristics of lignin polyols synthesized from "kraft" lignins and from organosolv lignins are set forth. Lignin polyols having an "E" designation are ethoxylated lignin polyols.

TABLE 3

Characteristics of lignin polyols

| Lignin Polyol | OH# (mg KOH/g) | Acid Value (mg KOH/g) | η, 25° C. (Pa · s) | Functionality (OH groups/mol fn (fw)) | Mn | Mw | Mw/Mn |
| --- | --- | --- | --- | --- | --- | --- | --- |
| Polyol-L-1 * | 495 | 1.64 | 46.6 | 7.6 (65) | 870 | 7900 | 9.04 |
| Polyol-L-2 * | 523 | 1.27 | 39.3 | 7.4 (69) | 800 | 7470 | 9.3 |
| Polyol-L-3 * | 497 | 1.53 | 21.6 | 7.0 (62) | 790 | 7000 | 8.8 |
| Polyol-L-4 E * | 491 | 1.30 | 20.1 | 7.9 (72) | 910 | 8300 | 9.1 |
| Polyol-L-5E * | 434 | 1.34 | 3.7 | 6.8 (61) | 890 | 7900 | 8.8 |
| Polyol-L-6** | 453 | 2.38 | 18.8 | 3.2 (28.6) | 397 | 3545 | 8.91 |
| Polyol-L-7E** | 390 | 1.3 | 5.6 | 3.2 (28.9) | 467 | 4170 | 8.92 |
| Polyol-L-8E** | 440 | 1.2 | 9.8 | 3.2 (28.9) | 410 | 3800 | 8.9 |

* "kraft" lignin;
**organosolv lignin;
fn = number average functionality
fw = weight average functionality Example 5

Synthesis of Ethoxylated Lignin Polyol

Lignin polyol produced in accordance with Example 4, was ethoxylated. Initially, the lignin polyol degassed to remove any remaining propylene oxide, and was then treated with about 13% by weight ethylene oxide (with the weight of the lignin poly fraction considered as 100% by weight) at 110-115° C. and 30-40 psi. No additional catalyst was necessary because the residual tetramethylguanidine in the lignin polyol remained active. After addition of the ethylene oxide was completed, as set forth in Example 4, the reaction mass was maintained at 110-115° C. for about 1-1.5 hours in order to complete the consumption of unreacted ethylene oxide. Finally, the last traces of remaining ethylene oxide were removed by vacuum distillation (60-65 mmHg and 110-115° C.).

The ethoxylated reaction product was a dark-brown viscous liquid, having a hydroxyl number of 398 mg KOH/g, an acid value of 1.30 mg KOH/g, a viscosity of 5.8 Pa·s at 25° C., a number average molecular weight (Mn) of 880, a weight average molecular weight (Mw) of 7800, and a polydispersity index (Mw/Mn) of 8.86.

We claim:

1. A process for the production of polyols comprising the steps of:
reacting a proteinaceous component selected from the group consisting of distillers grains, polyamides, and mixtures thereof, with a secondary amine under reaction conditions to generate amino-amides and amides; and
reacting said amino-amides and amides with an alkoxylating agent to generate polyols.

2. The process of claim 1, said distillers grains being dried distillers grains with solubles.

3. The process of claim 1, said amine selected from the group consisting of amines having the formula

wherein R1 and R2 are individually selected from the group consisting of C2-C12 straight and branched chain alkyl and alkenyl groups each having at least one hydroxyl group.

4. The process of claim 3, wherein R1 and R2 are selected from the group consisting of C2-C12 alkanols and alkenols.

5. The process of claim 4, each R1 and R2 being selected from the group consisting of C2-C4 alkanols.

6. The process of claim 5, each R1 and R2 being —CH2CH2OH.

7. The process of claim 1, said proteinaceous component comprising distillers grains, said distillers grains comprising dried distillers grains with solubles (DDGS), the ratio of said DDGS and said amine being from about 0.5-3.

8. The process of claim 7, said ratio being from about 1-1.2.

9. The process of claim 1, said proteinaceous component and said amine being reacted at a temperature of from about 150-250° C.

10. The process of claim 9, said temperature being from about 190-200° C.

11. The process of claim 1, said proteinaceous component and said amine being reacted at a pressure of from about 400-700 psi.

12. The process of claim 11, said pressure being from about 450-500 psi.

13. The process of claim 1, said alkoxylating agent selected from the group consisting of substituted and unsubstituted epoxides, and mixtures thereof.

14. The process of claim 13, said alkoxylating agent selected from the group consisting of epoxides having the formula

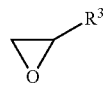

wherein R3 is selected from the group consisting of H, and C1-C6 straight or branched chain alkyl and alkenyl groups.

15. The process of claim 14, said alkoxylating agent being selected from the group consisting of propylene oxide, ethylene oxide, and mixtures thereof.

16. The process of claim 1, said amino-amide-alkoxylating agent reaction being carried out at a temperature of from about 80-150° C., and a pressure of from about 25-80 psi.

17. The process of claim 16, said amino-amide-alkoxylating agent reaction being carried out at a temperature of from about 100-120° C., and a pressure of from about 40-60 psi.

18. The process of claim 1, said proteinaceous component comprising protein.

19. The process of claim 18, said protein being a grain protein.

20. The process of claim 18, said protein being extracted from distillers grains.

21. A process for producing polyurethane, comprising the steps of:
reacting a proteinaceous component selected from the group consisting of distillers grains, polyamides, and mixtures thereof, with a secondary amine under reaction conditions to generate amino-amides;
reacting said amino-amides with an alkoxylating agent to generate polyols; and
reacting said polyols with isocyanate to generate polyurethane.

22. The process of claim 21, said distillers grains being dried distillers grains with solubles.

23. The process of claim 21, said amine, selected from the group consisting of amines having the formula

wherein R1 and R2 are individually selected from the group consisting of C2-C12 straight and branched chain alkyl and alkenyl groups each having at least one hydroxyl group.

24. The process of claim 23, wherein R1 and R2 are selected from the group consisting of C2-C12 alkanols and alkenols.

25. The process of claim 24, each R1 and R2 being selected from the group consisting of C2-C4 alkanols.

26. The process of claim 25, each R1 and R2 being —CH2CH2OH.

27. The process of claim 21, said proteinaceous component comprising distillers grains, said distillers grains comprising dried distillers grains with solubles (DDGS), the ratio of said DDGS and said amine being from about 0.5-3.

28. The process of claim 27, said ratio being from about 1-1.2.

29. The process of claim 21, said proteinaceous component and said amine being reacted at a temperature of from about 150-250° C.

30. The process of claim 29, said temperature being from about 190-200° C.

31. The process of claim 21, said proteinaceous component and said amine being reacted at a pressure of from about 400-700 psi.

32. The process of claim 31, said pressure being from about 450-500 psi.

33. The process of claim 21, said alkoxylating agent selected from the group consisting of substituted and unsubstituted epoxides, and mixtures thereof.

34. The process of claim 33, said alkoxylating agent selected from the group consisting of epoxides having the formula

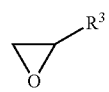

wherein R3 is selected from the group consisting of H, and C1-C6 straight or branched chain alkyl and alkenyl groups.

35. The process of claim 34, said alkoxylating agent being selected from the group consisting of propylene oxide, ethylene oxide, and mixtures thereof.

36. The process of claim 21, said proteinaceous component comprising protein.

37. The process of claim 36, said protein being a grain protein.

38. The process of claim 37, said protein being extracted from distillers grains.

39. A process for producing polyols comprising the steps of reacting lignin with an alkoxylating agent in the presence of a tertiary amine alkoxylation catalyst.

40. The process of claim 39, said alkoxylating agent selected from the group consisting of epoxides having the formula

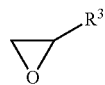

wherein R3 is selected from the group consisting of H, and C1-C6 straight or branched chain alkyl and alkenyl groups.

41. The process of claim 40, said alkoxylating agent being selected from the group consisting of propylene oxide, ethylene oxide, and mixtures thereof.

42. The process of claim 39, said reaction being carried out at a temperature of from about 100-120° C., and a pressure of from about 40-60 psi.

43. The process of claim 39, said lignin derived from distillers grains, wood, cooking liquors generated in wood pulp processing, and plants.

44. The process of claim 43, said lignin being a part of dried distillers grains with solubles.

45. A process for producing polyurethane, comprising the steps of:
   reacting lignin with an alkoxylating agent in the presence of a tertiary amine alkoxylation catalyst to generate polyols; and
   reacting said polyols with isocyanate to generate polyurethane.

46. The process of claim 45, said alkoxylating agent selected from the group consisting of epoxides having the formula

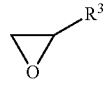

wherein R3 is selected from the group consisting of H, and C1-C6 straight or branched chain alkyl and alkenyl groups.

47. The process of claim 46, said alkoxylating agent being selected from the group consisting of propylene oxide, ethylene oxide, and mixtures thereof.

48. The process of claim 45, said reaction being carried out at a temperature of from about 100-120° C., and a pressure of from about 40-60 psi.

49. The process of claim 45, said lignin derived from distillers grains, wood, cooking liquors generated in wood pulp processing, and plants.

50. The process of claim 49, said lignin being a part of dried distillers grains with solubles.

51. The process of claim 45, said isocyanate being diisocyanate.

52. The process of claim 1, said reaction between said proteinaceous component and said secondary amine being conducted in a reaction medium comprising recycled polyols generated by a previous performance of said process.

53. The process of claim 1, said step of reacting said amino-amides and amides with said alkoxylating agent to generate polyols being conducted in the absence of a separately added catalyst.

54. The process of claim 21, said step of reacting said amino-amides and amides with said alkoxylating agent to generate polyols being conducted in the absence of a separately added catalyst.

55. The process of claim 39, said reaction between said lignin and said alkoxylating agent being conducted in a reaction medium comprising recycled polyols generated by a previous performance of said process.

* * * * *